United States Patent [19]
Robinson et al.

[11] Patent Number: 5,306,485
[45] Date of Patent: Apr. 26, 1994

[54] SUNCARE COMPOSITIONS

[75] Inventors: Larry R. Robinson, Oxford; Marie A. Rinaldi, Hamden; Anil J. Gupte, Seymour, all of Conn.

[73] Assignee: Richardson-Vicks Inc., Shelton, Conn.

[21] Appl. No.: 16,341

[22] Filed: Feb. 11, 1993

Related U.S. Application Data

[63] Continuation of Ser. No. 696,817, May 7, 1991, Pat. No. 5,207,998.

[51] Int. Cl.$^5$ .......... A61K 7/42; A61K 7/44; A61K 7/48; A61K 9/12
[52] U.S. Cl. .......... 424/59; 424/DIG. 5; 424/47; 424/60; 514/167; 514/251; 514/458; 514/474; 514/844; 514/847; 514/873; 514/937; 514/938; 514/944
[58] Field of Search .......... 424/59

[56] References Cited

U.S. PATENT DOCUMENTS

| | | | |
|---|---|---|---|
| 4,172,122 | 10/1979 | Kubik et al. | 424/59 |
| 4,597,963 | 7/1986 | Deckner | 424/59 |
| 4,603,046 | 7/1986 | Georgalas et al. | 424/59 |
| 4,663,157 | 5/1987 | Brock | 424/59 |
| 4,671,955 | 6/1987 | Palinczar | 424/59 |
| 4,683,134 | 7/1987 | Palinczar | 424/59 |
| 4,686,009 | 8/1987 | Palinczar | 424/47 |
| 4,699,779 | 10/1987 | Palinczar | 424/59 |
| 4,710,371 | 12/1987 | Palinczar | 424/47 |
| 4,731,242 | 3/1988 | Palinczar | 424/59 |
| 4,781,914 | 11/1988 | Deckner | 424/59 |
| 4,810,489 | 3/1989 | Murray et al. | 424/59 |
| 4,810,490 | 3/1989 | Dixon et al. | 424/59 |
| 4,917,882 | 4/1990 | Strobridge | 424/59 |
| 4,917,883 | 4/1990 | Strobridge | 424/59 |
| 4,919,934 | 4/1990 | Deckner et al. | 424/401 |
| 5,207,998 | 5/1993 | Robinson et al. | 424/59 |

FOREIGN PATENT DOCUMENTS 14124924  4/1985  Australia .......... 424/59

*Primary Examiner*—Dale R. Ore
*Attorney, Agent, or Firm*—Anthony D. Sabatelli; David K. Dabbiere

[57] ABSTRACT

Disclosed are sunscare compositions having enhanced substantivity, efficacy and the like for protecting the skin from the harmful effects of ultraviolet irradiation, such as sunburn and sun-induced premature aging of the skin.

20 Claims, No Drawings

SUNCARE COMPOSITIONS

This is a continuation of application Ser. No. 696,817, filed on May 7, 1991, now U.S. Pat. No. 5,207,998.

TECHNICAL FIELD

This invention relates to topical suncare compositions having enhanced substantivity, efficacy and the like for providing protection from the harmful effects of ultraviolet radiation, such as sunburn and sun-induced premature aging of the skin. Specifically, these compositions contain octocrylene and titanium dioxide as the principal sunscreen active ingredients in a safe and effective amount of a topical carrier.

BACKGROUND OF THE INVENTION

The damaging effects of sunlight on skin are well documented. Contrary to what most people believe, it is not necessary that one sunbathe to suffer the ill-effects of excessive UV exposure. In fact, significant damage can be done just by routine day-today activities in the sunlight. Some scientists estimate that over 70 percent of the damage the sun inflicts on the average person's skin over a lifetime is the result of simply being outdoors or even sitting by a window.

The major short term hazard of prolonged exposure to sunlight is erythema (i.e. sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard or erythema, there are also long term hazards associated with UV radiation exposure. One of these long term hazards is malignant changes in the skin surface. Numerous epidemiologic studies demonstrate a strong relationship between sunlight exposure and human skin cancer.

Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed. , Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued Jun. 7, 1983; the disclosures of all of which are incorporated herein by reference. Hence, although the immediate effects of ultraviolet radiation may be cosmetically and socially gratifying, the long-term hazards are cumulative and potentially serious. It has been estimated that eighty percent of lifetime sun exposure occurs during multiple brief exposures not intended to produce tanning. Therefore, photoprotection during these exposures to ultraviolet radiation is necessary.

The fact that these effects are taken seriously by the general public is suggested by considering the sun protection products' market. This market has grown considerably in recent years and many new products are introduced each year. What used to be looked upon as a seasonal business is no longer. Sun protection compounds are now included in a diversity of personal care products, particularly cosmetic-type products which are worn on a daily basis.

Physical sunblock agents are commercially available to protect the skin from UV radiation. These agents scatter, reflect, and absorb ultraviolet radiation. See, Sayre, R. M. et. al., "Physical Sunscreens", *J. Soc. Cosmet. Chem.*, vol. 41, no.2, pp. 103–109 (1990). Examples of physical sunblock agents include titanium dioxide and zinc oxide. However, compositions containing a high level of these agents are opaque, generally unattractive in color, and are viewed as unacceptable for usage on more than just the nose or tops of the ears. Furthermore, these agents are very susceptible to rub-off or wear-off resulting in little or no protection. Therefore, it would be highly desirable to develop compositions containing physical sunblock agents such as titanium dioxide which do not suffer from these disadvantages.

The most common agents for sun protection are sunscreens. These agents exert their effects through chemical means, i.e., they absorb ultraviolet radiation so that it cannot penetrate the skin. Sunscreens present the user with several problems. For example, they must be on the surface of the skin at the time of exposure to be effective. Sunscreens are preventative so one must anticipate being in the sun. To be most effective, sunscreens must be on the skin as a continuous uniform film. Delivering such a film to the uneven surface of the skin is very difficult.

Sunscreen formulations based on oil-in-water emulsions are the most popular form of photoprotection products in the U.S. market. This form is cosmetically pleasing, safe, cost effective and versatile. In general, however, oil-in-water emulsions containing oil-soluble sunscreens do not provide as good sunscreening efficiency when compared to water-in-oil emulsions containing oil soluble sunscreens.

Without being limited by theory, it is believed that the specific compositions of the present invention having a mixture of octocrylene and titanium dioxide as the sunscreen component, provide synergistic benefits such as improved substantivity as well as increased UV absorption. These synergistic benefits are readily apparent when UV absorption data on formulations containing this sunscreen mixture are compared to either those not containing this mixture or to the theoretical sum of the individual sunscreen components, as determined from mean percentage absorption data. The compositions of the present invention further provide reduced sunscreen migration thereby reducing, for example, eye-stinging, by inhibiting the sunscreen active from invading the eye area.

It is therefore an object of the present invention to provide a topical composition in a stable form, the use of which will prevent both acute (erythema) and chronic (photoaging) effects of exposure to the sun and other sources of ultraviolet radiation.

It is a further object of the present invention to provide suncare compositions having enhanced substantivity, efficacy and the like having a sunscreen component consisting essentially of octocrylene and titanium dioxide.

It is an even further object of the present invention to provide suncare compositions in the form of oil-in-water emulsions which have a surface tension of greater than about 30 dynes/cm, when measured on a 3.3% (w/w) aqueous solution of the emulsion, which possess a wax component having a required HLB between about 1 and about 8.

It is a still further object of the present invention to provide a method for enhanced protection of the skin of humans or lower animals from the effects of ultraviolet radiation.

These and other objects will become readily apparent from the detailed description that follows.

SUMMARY OF THE INVENTION

The present invention relates to a suncare composition having enhanced substantivity, efficacy and the like, comprising:

(a) a sunscreen component consisting essentially of:
 (i) from about 0.1% to about 20% of octocrylene based on the weight of the total composition; and
 (ii) from about 0.1% to about 25% of titanium dioxide based on the weight of the total composition; and (b) a safe and effective amount of a topical carrier.

The present invention further relates to a method for providing enhanced protection to the skin of humans or lower animals from the effects of ultraviolet radiation.

All percentages and ratios used herein are by weight of the total composition and all measurements made at 250° C., unless otherwise designated.

DETAILED DESCRIPTION OF THE INVENTION

The present invention provides suncare compositions comprising a sunscreen component and a safe and effective amount of a cosmetically acceptable topical carrier for providing protection against harmful UV radiation. The sunscreen component of the present invention consists essentially of octocrylene and titanium dioxide.

Octocrylene

Octocrylene is an essential element of the sunscreen component of the present invention. Octocrylene, which is also known as 2-ethylhexyl 2-cyano-3,3-diphenylacrylate or 2-ethylhexyl 2-cyano-3,3-diphenyl-2-propenoate, is a viscous yellowish liquid having a freezing point of approximately $-10°$ C. octocrylene is further described in U.S. Pat. No. 3,215,724, to Strobel et al., issued Nov. 2, 1965; and BASF Provisional Technical Leaflet, "Uvinul® Grades: UV Absorber for Cosmetic Products"; both of these references are incorporated herein by reference in their entirety. Octocrylene is commercially available as Uvinul N ® 539 from BASF (Ludwigshafen, West Germany).

The octocrylene is present from about 0.1% to about 20% of the total weight of the compositions of the instant invention, preferably from about 3% to about 10%., and more preferably from about 3% to about 7%.

Titanium Dioxide

Titanium dioxide is an essential element of the sunscreen component of the instant invention. The titanium dioxide useful in the present invention can have an anatase, rutile, or amorphous structure. The titanium dioxide useful in the present invention preferably has a mean particle size from about 1 nm to about 100 nm, more preferably from about 15 nm to 50 nm, and most preferably from about 30 to 50 nm. The titanium dioxide particles can be uncoated or can be coated with a variety of materials including, but not limited to, aluminum compounds such as aluminum oxide, aluminum stearate, aluminum laurate and the like; phospholipids such as lecithin; silicone compounds; and mixtures thereof. Various grades and forms of titanium dioxide are described in *CTFA Cosmetic Ingredient Dictionary*, Third Edition (1982), pp. 318–319; U.S. Pat. No. 4,820,508 to Wortzman, issued Apr.11, 1989; and World Patent No. WO 90/11067 to Elsom et al, published Oct. 4, 1990; these three references are incorporated by reference herein in their entirety.

Suitable grades of titanium dioxide for use in the compositions of the present invention are available commercially such as the MT micronized series from Tri-K Industries (Emerson, NJ). These micronized titanium dioxides generally have a mean primary particle size ranging from about 10 nm to about 50 nm. For example, titanium dioxide having a mean primary particle size of about 15 nm is available under the trade designations MT-150W (uncoated) and MT-100T (coated with stearic acid and aluminum compounds). Uncoated titanium dioxides having mean primary particle sizes of around 35 nm and around 50 nm are available under the trade designations MT-500B and MT-600B, respectively. Other coated titanium dioxides having a mean primary particle size around 15 nm include MT-100F (modified with stearic acid and iron hydroxide) and MT-100S (treated with lauric acid and aluminum hydroxide). Mixtures of two or more types and particle size variations of titanium dioxide can be used in the present invention.

The titanium dioxide is present from about 0.1% to about 25% of the weight of the total composition, more preferably from about 0.5% to about 5%, and most preferably from about 1% to about 4%.

Ratio of Octocrylene to Titanium Dioxide

The ratio of octocrylene to titanium dioxide in the sunscreen component of the instant invention ranges from about 100:1 to about 1:0.25, preferably from about 70:1 to about 3:1, and more preferably from about 10:1 to about 3:1. An especially preferred ratio is about 7:1.

Topical Carriers

The compositions of the instant invention comprise as a necessary component a safe and effective amount of a topical carrier or diluent which can be of a variety of different forms. By "safe and effective" is meant an amount sufficient to act as a suitable vehicle for the octocrylene, titanium dioxide and any other components, but not so much as to cause any side effects or skin reactions. The topical carrier can be in the form of an emulsion including, but not limited to, oil-in-water, water-in-oil, water-in-oil-in-water, and oil-in-water-in-silicone emulsions. These emulsions can cover a broad range of consistencies including thin lotions (which can also be suitable for spray or aerosol delivery), creamy lotions, light creams, heavy creams, and the like. Other suitable topical carriers include an hydrous liquid solvents such as oils and alcohols; aqueous-based single phase liquid solvents (e.g. hydro-alcoholic solvent systems); anhydrous solids and semisolids (such as gels and sticks); and aqueous based gel and mousse systems. Examples of topical carrier systems useful in the present invention are described in the following four references all of which are incorporated herein by reference in their entirety: "Sun Products Formulary" *Cosmetics & Toiletries*, vol. 105, pp. 122–139 (December 1990); "Sun Products Formulary", *Cosmetics & Toiletries*, vol. 102, pp. 117-136 (March 1987); U.S. Pat. No. 4,960,764 to Figueroa et al., issued Oct. 2, 1990; and U.S. Pat. No. 4,254,105 to Fukuda et al., issued Mar. 3, 1981.

The pharmaceutically-acceptable topical carriers, in total, typically comprise from about 0.1% to about 99.87. by weight of the sunscreen compositions of the present invention, preferably from about 80% to about 99%, and most preferably from about 85% to about 95%.

A preferred topical carrier of the compositions of the instant invention is an oil-in-water type emulsion. The pH of these oil-in-water emulsion compositions herein is preferably in the range of from about 4.5 to about 9. Additionally, the mean particle size of the dispersed oil phase materials (e.g., sunscreen agent, polymer, perfumes, etc.) dispersed in the aqueous phase of these oil-in-water emulsion compositions may be in the range of from about 5 to about 10 microns with greater than about 75% of the particles being less than about 12 microns.

Surface Tension

The surface tension of the compositions of the present invention are determined experimentally as 1%-50% (W/w) aqueous solutions using a Kruss model no. K12 processor tensiometer (available from Kruss, W.Germany). The measurements are made at 25° C. using either the Wilhelmy plate method at a dipping distance of 1 mm or the Du Nouy ring method, with a return distance of 3.33% and a margin searching value of 1 mg. Preferably the surface tension measurements are determined as 3.33% (w/w) aqueous solutions using the Wilhelmy plate method.

When the compositions of the instant invention are in the form of an oil-in-water emulsion, i.e. when the topical carrier is an oil-in-water emulsion, the surface tension of the composition, when diluted as a 3.33% (w/w) aqueous solution has a surface tension greater than about 30 dynes/cm, preferably greater than about 31 dynes/cm, and most preferably greater than about 32 dynes/cm.

Solubility Parameters of Oil Phase Components

The "oil phase components" of the compositions of the instant invention are those ingredients which are generally non-polar and have limited solubility in water.

The oil phase components of the present invention are herein defined to include the sunscreens (such as ethylhexyl-p-methoxycinnamte), waxes (such as stearoxy trimethylsilane/stearyl alcohol, and tristearin), esters (such as isoarchidyl neopentanoate), preservatives (such as propylparaben), substantivity and film-forming copolymers (such as polyvinylpyrollidone/eicosene copolymer), hydrocarbons, and other suitable materials.

For the instant invention, when the topical carrier is an oil-in-water emulsion, the weighted average of the calculated solubility parameters of the oil phase components is preferably from about 6.0 to about 9.0.

The solubility parameter of a material, δ, is defined as the square root of the cohesive energy density for that material. Knowing the chemical structure of a material, the solubility parameter is readily calculated from the additive group contributions for heat of vaporization and molar volume as shown by equation (1).

$$\delta = \left[ \frac{\sum_i E_i}{\sum_i m_i} \right]^{\frac{1}{2}} \quad \text{equation (1)}$$

The additive group contributions for heat of vaporization and molar volume used to calculate the solubility parameters of the present invention are tabulated in Barton, A.F.M. *Handbook of Solubility Parameters*, CRC Press, Chapter 6, Table 3, pp. 64-66 (1985). The relationship of equation (1) is described in Fedors, R. F., "A Method for Estimating Both the Solubility Parameters and Molar Volumes of Liquids", *Polymer Engineering and Science*, vol. 14, no. 2, pp. 147-154 (February 1974), these two publications being incorporated herein by reference.

Calculated solubility parameters obey the law of mixtures such that the calculated solubility parameter for a mixture of materials is given by the weighted average of the calculated solubility parameters for each component of that mixture. See, *Handbook of Chemistry and Physics*, 57th edition, CRC Press, p. C-726 (1976-1977), this publication being incorporated herein by reference.

All calculated solubility parameters of the present invention are reported in units of $(cal/CM^3)^{\frac{1}{2}}$. The tabulated values for the additive group contributions for heat of vaporization in the *Handbook of Solubility Parameters* are reported in units of kj/mol. These values are converted to cal/mol using the relationships:

1 J/mol = 0.239006 cal/mol and 1000 J = 1 kJ.

See Gordon, A. J. et al., *The Chemist's Companion*, John Wiley & Sons, pp. 456-463, (1972), this publication being incorporated herein by reference.

Optional Components

The compositions of the instant invention can also contain the following optional components.

Additional Sunscreens

The compositions of the present invention can optionally contain from about 0.5% to about 20% of one or more additional sunscreen agents. Sagarin, et al., at Chapter VIII, pages 189 et seq., of *Cosmetics Science and Technology*, disclose numerous suitable agents. Specific suitable sunscreening agents include, for example: p-Aminobenzoic acid, its salts and its derivatives (ethyl, isobutyl, glyceryl esters; p-dimethylaminobenzoic acid); Octyl Methoxycinnamate (i.e. ethylhexyl-p-methoxycinnamate); Anthranilates (i.e., o-aminobenzoates; methyl, octyl, amyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); 2-Phenylbenzimidazole-5-sulfonic acid; Cinnamic acid derivatives (menthyl and benzyl esters, -phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene,,stilbene); Dibenzalacetone and benzalacetophenone; Naphtholsulfonates (sodium salts of 2-naphthol 3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; 4-isopropyl-di-benzoylmethane; and camphor derivatives such as methyl benzylidene or benzylidene camphor; and mixtures thereof. Other sunscreens include the solid physical sunblocks such as zinc oxide, silica, iron oxide and the like. Without being limited by theory, it is believed that these inorganic materials provide a sunscreening benefit through reflecting, scattering, and absorbing harmful UV, visible, and infrared radiation.

A safe and photoprotectively effective amount of an additional sunscreen may be used in the sunscreen compositions of the present invention. By "safe and photoprotectively" is meant an amount sufficient to provide photoprotection when the composition is applied, but not so much as to cause any side effects or skin reactions. Generally, the additional sunscreen agent(s) can comprise from about 0.5% to about 20% of the composition. Exact amounts will vary depending upon the sunscreen chosen and the desired Sun Protection Factor (SPF).

SPF is a commonly used measure of photoprotection of a sunscreen against erythema. This number is derived from another parameter, the minimal erythemal dose (MED). MED is defined as the "least exposure dose at a specified wavelength that will elicit a delayed erythema response". The MED indicates the amount of energy reaching the skin and the responsiveness of the skin to the radiation. The SPF of a particular photoprotector is obtained by dividing the MED of protected skin by the MED of unprotected skin. The higher the SPF, the more effective the agent in preventing sunburn. The SPF value tells how many times longer a person can stay in the sun with use of the sunscreen (compared to the same person with unprotected skin) before that person will experience I MED. For example, utilizing a sunscreen with an SPF of 6 will allow an individual to stay in the sun six times longer before receiving I MED. As the SPF value of a sunscreen increases, the less chance exists for development of tanning of the skin. Commercially available sunscreening products have SPF values ranging from 2 to 50. The compositions of the present invention preferably provide an SPF value of at least 8.

Also particularly useful along with the sunscreen component of the present invention are those sunscreens disclosed in U.S. Pat. No. 4,937,370, to Sabatelli, issued Jun. 26, 1990; and U.S. Pat. No. 4,999,186 to Sabatelli et al., issued Mar. 12, 1991. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone, and N,N-di-(2-ethylhexyl)4-aminobenzoic acid ester of 4-(2-hydroxyethoxy)dibenzoylmethane and mixtures thereof.

Emulsifiers

Another optional component of the compositions of the instant invention is at least one emulsifier. Suitable emulsifiers can include any of a wide variety of nonionic, cationic, anionic, and zwitterionic emulsifiers disclosed in the prior patents and other references. See McCutcheon's, *Detergents and Emulsifiers,* North American Edition (1986), published by Allured Publishing Corporation; U.S. Pat. No. 5,011,681 to Ciotti et al, issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof.

The emulsifiers can be used individually or as a mixture of two or more and comprise from about 0.1% to about 10%, preferably from about 1% to about 7%, and most preferably from about 1% to about 5% of the compositions of the present invention.

Carboxylic Acid Copolymer

The compositions of the present invention can optionally contain at least one emulsifier comprising a carboxylic acid copolymer (i.e. an acrylic acid copolymer). These copolymers consist essentially of a colloidally water-soluble polymer of acrylic acid crosslinked with a polyalkenyl polyether of a polyhydric alcohol, and optionally an acrylate ester or a polyfunctional vinylidene monomer.

Preferred carboxylic acid copolymers useful in the present invention are polymers of a monomeric mixture containing 95.9 to 98.8 weight percent of an olefinically unsaturated carboxylic monomer selected from the group consisting of acrylic, methacrylic and ethacrylic acids; about 1 to about 3.5 weight percent of an acrylate ester of the formula:

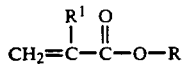

wherein R is an alkyl radical containing 10 to 30 carbon atoms and $R^1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R^1$ is methyl, most preferably the acrylate ester is stearyl methacrylate. Preferably, the amount of cross-linking polyalkenyl polyether monomer is from about 0.2 to 0.4 weight percent. The preferred crosslinking polyalkenyl polyether monomers are allyl pentaerythritol, trimethylolpropane diallylether or allyl sucrose. These polymers are fully described in U.S. Pat. 4,509,949, to Huang et al., issued Apr. 5, 1985, this patent being incorporated herein by reference.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials may be present in the monomeric mixture if desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

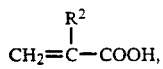

wherein $R^2$ is a substituent selected from the class consisting of hydrogen, halogen, and the cyanogen (—C≡N) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The second monomeric ingredient useful in the production of these carboxylic polymers are the polyalkenyl polyethers having more than one alkenyl ether grouping per molecule. The most useful possess alkenyl groups in which an olefinic double bond is present attached to a terminal methylene grouping, $CH_2=C<$.

The additional monomeric materials which may be present in the polymers include polyfunctional vinylidene monomers containing at least two terminal $CH_2<$ groups, including, for example, butadiene, isoprene, divinyl benzene, divinyl naphthalene, allyl acrylates, and the like. These polymers are fully described in U.S. Pat. No. 2,798,053, to Brown, H. P., issued Jul. 2, 1957, this patent being incorporated herein by reference.

Examples of carboxylic acid copolymers useful in the present invention include Carbomer 934, Carbomer 941, Carbomer 950, Carbomer 951, Carbomer 954, Carbomer 980, Carbomer 981, Carbomer 1342, and Acrylates/$C_{10-30}$ Alkyl Acrylate Cross Polymers (available as Carbopol 934, Carbopol 941, Carbopol 950, Carbopol 951, Carbopol 954, Carbopol 980, Carbopol 981, Carbopol 1342, and the Pemulen series, respectively, from B. F. Goodrich).

Other carboxylic acid copolymers useful in the present invention include sodium salts of acrylic acid/acrylamide copolymers sold by the Hoechst Celanese Corporation under the trademark of Hostaceren PN73. Also included are the hydrogel polymers sold by Lipo Chemicals Inc. under the trademark of HYPAN hydrogels. These hydrogels consist of crystalline plicks of nitriles on a C—C backbone with various other pendant groups such as carboxyls, amides, and amidines. An example would include HYPAN SA100 H, a polymer powder available from Lipo Chemical.

Neutralizing agents suitable for use in neutralizing acidic group containing copolymers herein include sodium hydroxide, potassium hydroxide, ammonium hydroxide, monoethanolamine, diethanolamine, triethanolamine, tetrahydroxypropyl ethylenediamine (available as the Quadrol ® series from BASF), tris, arginine, triisopropylamine and lysine.

The carboxylic acid copolymers can be used individually or as a mixture of two or more polymers and comprise from about 0.025 to about 0.75, preferably from about 0.05 to about 0.25 and most preferably from about 0.075 to about 0.175 percent of the compositions of the present invention.

Wax Component

Another optional component of the compositions herein is a non-polar wax component having a required HLB of from about 1 to about 8, more preferably from about 1 to about 7 and a melting point greater than about 50° C., and preferably greater than about 60° C.

Useful waxes include ester waxes, diester waxes, hydrocarbon waxes, silicone waxes and triglyceride waxes and mixtures thereof.

It is important that the HLB measurements be determined experimentally rather than from empirical calculations. The HLB (short for "Hydrophile-Lipophile Balance") value system is fully described, and values for various materials are provided, in the publication *The HLB System, A Time-Saving Guide to Emulsifier Selection* (published by ICI Americas Inc., Wilmington, Delaware; 1984), the disclosures of which are incorporated herein by reference in their entirety.

Useful ester waxes include $C_{16}$–$C_{40}$ alcohols esterfied with $C_{16}$–$C_{40}$ fatty acid, diesters Of $C_{16}$–$C_{40}$ fatty acid where the alcohol is propylene glycol, ethylene glycol, polyethylene glycol, polypropylene glycol, $C_{12}$–$C_{40}$, triglycerides or $C_{18}$–$C_{40}$ diglycerides, pentaerythitol tri- or tetra- esters of $C_{12}$–$C_{40}$ fatty acids, $C_{18}$–$C_{40}$ fatty acids of sorbitan triesters. Useful synthetic waxes include Fischer-Tropsche waxes. Useful hydrocarbon waxes include paraffin, microcrystalline waxes, and mixtures thereof. Useful diester waxes include Syncrowax ERL-C (available from Croda); $C_{18}$–$C_{40}$ fatty acid diester and propylene glycol diester waxes including propylene glycol distearate and glycol distearate. Useful triglyceride waxes include Syncrowax HGL-C, Syncrowax HRC, Syncrowax HRS-C (all available from Croda Inc.), tristearin, trimyristate, castor wax and fully hydrogenated vegetable or animal oils as well as alkyloxysilicone waxes (such as Dow Corning 580 Wax) and mixtures thereof.

Those waxes those useful in the compositions of this invention are disclosed in the following, all of which are incorporated by reference herein in their entirety: U.S. Pat. No. 4,049,792, to Elsnau, issued Sep. 20, 1977; U.S. Pat. No. 4,151,272, to Geary et al., issued Apr. 24, 1975; U.S. Pat. No. 4,229,432, to Geria, issued Oct. 21, 1980; U.S. Pat. No. 4,280,994, to Turney, issued Jul. 28, 1981; U.S. Pat. No. 4,126,679, to Davy et al., issued Nov. 21, 1978; and European Patent Application Publication Number 117,070, to May, published Aug. 29, 1984, "The Chemistry and Technology of Waxes", A. H. Warth, 2nd Edition, reprinted in 1960, Reinhold Publishing Corporation, pp 391–393 and 421; "The Petroleum Chemicals Industry", R. F. Goldstein and A. L. Waddeam, 3rd Edition (1967), E. & F. N. Span Ltd., pp 33–40; "The Chemistry and Manufacture of Cosmetics", M. G. DeNavarre, 2nd edition (1970), Van Nostrand & Company, pp 354–376; and in "Encyclopedia of Chemical Technology", Vol. 24, Kirk-Othmer, 3rd Edition (1979) pp 466–481.

Film-forming Copolymer

The compositions of the present invention also optionally contain a film-forming copolymer at a level of from about 0.1% to about 5.0%, preferably from about 0.1% to about 2%.

A preferred film-forming copolymer is of the formula:

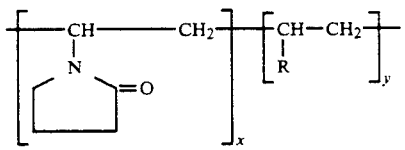

where R is a $C_{12}$–$C_{30}$ straight chain alkyl and preferably a $C_{18}$–$C_{22}$ straight chain alkyl and wherein the ratio of x to y is from about 1:5 to about 5:1. A particularly preferred copolymer is I-eicosene polymer with 1-ethenyl-2-pyrrolidinone available from GAF Chemical Corporation as Ganex V-220 ®.

Vitamins

Optionally, various vitamins can also be included in the compositions of the present invention. Non-limiting examples include Vitamin A, and derivatives thereof, ascorbic acid, Vitamin B, biotin, Vitamin D, Vitamin E and derivatives thereof such as tocopheryl acetate, panthothenic acid, and mixtures thereof can also be used.

Humectants/Moisturizers

The compositions of the instant invention can also optionally contain one or more humectants/moisturizers. A variety of humectants/moisturizers can be employed and can be present at a level of from about 1% to about 30%, more preferably from about 2% to about 8% and most preferably from about 3% to about 5%. These materials include urea; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerin, hexanetriol, propylene glycol, hexylene glycol and the like; polyethylene glycol; sugars and starches; sugar and starch derivatives (e.g. alkoxylated glucose); D-panthenol; hyaluronic acid; lactamide monoethanolamine; acetamide monoethanolamine; and mixtures thereof.

Preferred humectants/moisturizers for use in the compositions of the present invention are the $C_3$–$C_6$ diols and triols. Especially preferred is the triol, glycerin.

Emollients

The compositions of the present invention can also optionally comprise at least one emollient. Examples of suitable emollients include, but are not limited to, volatile and non-volatile silicone oils, highly branched hydrocarbons, and non-polar fatty acid and fatty alcohol esters, and mixtures thereof. Emollients useful in the instant invention are further described in U.S. Pat. No. 4,919,934, to Deckner et al., issued Apr. 24 1990, which is incorporated herein by reference in its entirety.

The emollients can typically comprise in total from about 1% to about 50%, preferably from about 1% to about 25%, and more preferably from about 1% to about 10% by weight of the compositions of the present invention.

Other Optional Components

A variety of additional ingredients can be incorporated into the emulsion compositions of the present invention. Non-limiting examples of these additional ingredients include various polymers for aiding the film-forming properties and substantivity of the formulation; gums, resins, and thickeners; preservatives for maintaining the antimicrobial integrity of the compositions; antioxidants; chelators and sequestrants; and agents suitable for aesthetic purposes such as fragrances, pigments, and colorings.

EXAMPLES

The following non-limiting examples illustrate embodiments of the subject invention wherein both essential and optional ingredients are combined. It is to be understood that these examples are for illustrative purposes only and are not to be construed as limiting the scope of the invention thereto.

Ingredients are identified by chemical or CTFA name.

Example I

Sunscreen Cream

An oil-in-water emulsion is prepared by combining the following components utilizing conventional mixing techniques.

| Ingredients | % Weight |
| --- | --- |
| Phase A | |
| Water | QS100 |
| Carbomer 954[1] | 0.24 |
| Carbomer 1342[2] | 0.16 |
| Disodium EDTA | 0.05 |
| Phase B | |
| Isoarachidyl Neopentanoate[3] | 2.00 |
| PVP Eicosene Copolymer[4] | 2.00 |
| Octocrylene | 7.00 |
| Titanium Dioxide | 1.00 |
| Cetyl Palmitate | 0.75 |
| Stearoxytrimethylsilane (and) Stearyl Alcohol[5] | 0.50 |

-continued

| Ingredients | % Weight |
|---|---|
| Glyceryl Tribehenate[6] | 0.75 |
| Dimethicone | 1.00 |
| Tocopheryl Acetate | 0.10 |
| DEA-Cetyl Phosphate | 0.20 |
| Phase C | |
| Water | 2.00 |
| Triethanolamine 99% | 0.60 |
| Phase D | |
| Water | 2.00 |
| Butylene Glycol | 2.00 |
| DMDM Hydantoin (and) Iodopropynyl Butylcarbamate[7] | 0.25 |
| dL Panthenol | 1.00 |
| Phase E | |
| Cyclomethicone | 1.00 |

[1] Available as Carbopol ® 954 from B.F. Goodrich.
[2] Available as Carbopol ® 1342 from B.F. Goodrich.
[3] Available as Elefac I-205 from Bernel Chemical.
[4] Available as Ganex V-220 from GAF Corporation.
[5] Available as DC 580 Wax from Dow Corning.
[6] Available as Synchrowax HRC from Croda.
[7] Available as Glydant Plus from Lonza.

In a suitable vessel the Phase A ingredients are dispersed in the water and heated to 75°–85° C. In a separate vessel the Phase B ingredients (except DEA-Cetyl Phosphate) are combined and heated to 85°–90° C. until melted. Next, the DEA-Cetyl Phosphate is added to the liquid Phase B and stirred until dissolved. This mixture is then added to Phase A to form the emulsion. The Phase C ingredients are combined until dissolved and then added to the emulsion. The emulsion is then cooled to 40°–45° C. with continued mixing. In another vessel, the Phase D ingredients are heated with mixing to 40°–45° C. until a clear solution is formed and this solution is then added to the emulsion. Finally, the emulsion is cooled to 35° C. and the Phase E ingredient is added and mixed.

This emulsion is useful for topical application to the skin to provide protection from the harmful effects of ultraviolet radiation.

EXAMPLE II

Sunscreen Cream

An oil-in-water emulsion is prepared by combining the following components utilizing conventional mixing techniques.

| Ingredients | % Weight |
|---|---|
| Phase A | |
| Water | QS100 |
| Carbomer 954 | 0.14 |
| Acrylates/C$_{10-30}$ Alkyl Acrylate Crosspolymer[1] | 0.16 |
| Disodium EDTA | 0.05 |
| Phase B | |
| Isohexadecane[2] | 2.00 |
| PVP Eicosene Copolymer | 2.00 |
| Octocrylene | 7.00 |
| Titanium Dioxide | 3.00 |
| Cetyl Palmitate | 0.75 |
| Stearoxytrimethylsilane (and) Stearyl Alcohol | 0.50 |
| Glyceryl Tribehenate | 0.75 |
| Dimethicone | 1.00 |
| Tocopheryl Acetate | 0.10 |
| DEA-Cetyl Phosphate | 0.20 |
| Phase C | |
| Water | 2.00 |
| Triethanolamine 99% | 0.40 |
| Phase D | |

| Ingredients | % Weight |
|---|---|
| Water | 2.00 |
| Butylene Glycol | 1.00 |
| DMDM Hydantoin (and) Iodopropynyl Butylcarbamate | 0.25 |
| dL Panthenol | 1.00 |
| Phase E | |
| Cyclomethicone | 1.00 |

[1] Available as Pemulan TR-1 from B.F. Goodrich.
[2] Available as Permethyl/101A from Presperse, Inc. (South Plainfield, NJ).

An emulsion is prepared from the above ingredients employing the method described in Example I.

This emulsion is useful for topical application to the skin to provide protection from the harmful effects of ultraviolet radiation.

EXAMPLE III

Sunscreen Lotion

An oil-in-water emulsion is prepared by combining the following components utilizing conventional mixing techniques.

| Ingredients | % Weight |
|---|---|
| Phase A | |
| Water | QS100 |
| Carbomer 954 | 0.15 |
| Carbomer 1342 | 0.10 |
| Disodium EDTA | 0.05 |
| Phase B | |
| Isoarachidyl Neopentanoate | 2.00 |
| Octocrylene | 7.00 |
| Titanium Dioxide | 1.00 |
| Cetyl Palmitate | 0.75 |
| Stearoxytrimethylsilane (and) Stearyl Alcohol | 0.50 |
| Glyceryl Tribehenate | 0.75 |
| DEA-Cetyl Phosphate | 0.20 |
| Phase C | |
| Water | 2.00 |
| Triethanolamine 99% | 0.31 |
| Phase D | |
| Water | 2.00 |
| Butylene Glycol | 2.00 |
| DMDM Hydantoin (and) Iodopropynyl Butylcarbamate | 0.25 |
| Glycerin | 2.00 |

An emulsion is prepared from the above ingredients employing a method analogous to that described in Example I, except that the preparation is complete after the addition of the phase D ingredients.

This emulsion is useful for topical application to the skin to provide protection from the harmful effects of ultraviolet radiation.

EXAMPLE IV

Soap-Based Sunscreen Emulsion Cream

A soap-based sunscreen emulsion is prepared by combining the following components.

| Ingredients | % Weight |
|---|---|
| Phase A | |
| Water | QS100 |
| Carbomer 940 | 0.50 |
| Propylene Glycol | 3.00 |
| Methylparaben | 0.20 |
| Phase B | |

-continued

| Ingredients | % Weight |
| --- | --- |
| Stearic Acid | 3.00 |
| Glyceryl Stearate and PEG-100 Stearate | 3.00 |
| Cetyl Alcohol | 0.50 |
| Lanolin | 1.00 |
| PVP/Eicosene Copolymer | 2.00 |
| Octocrylene | 7.00 |
| Titanium Dioxide | 1.00 |
| Phase C | |
| Triethanolamine | 0.80 |
| Phase D | |
| Water | 2.00 |
| Imidazolidinyl Urea | 0.30 |
| Phase E | |
| Dimethicone | 2.00 |
| Diazolidinyl Urea | 0.30 |
| Aloe Vera | 0.50 |
| Fragrance | 0.10 |

Begin heating the water of Phase A to 80° C., sift carbomer into water with constant agitation. Add rest of Phase A ingredients and mix until clear. Heat Phase B ingredients to 80° C. and add to Phase A to form the emulsion. Add Phase C and mix until smooth and cool to 40° C. Mix Phase D ingredients until clear and add to the emulsion. Cool to room temperature. Slowly add Phase E ingredients and mix until uniform.

This sunscreen emulsion is useful for topical application to the skin to provide protection from the harmful effects of ultraviolet radiation.

EXAMPLE V

Rich Water-in-Oil Sunscreen Emulsion Cream

| Ingredients | % Weight |
| --- | --- |
| Phase A | |
| PEG-6 Beeswax Esters (and) Polyglyceryl Isostearate (and) PEG-6 Stearate[1] | 12.00 |
| Beeswax | 1.00 |
| Mineral Oil | 15.00 |
| Octyl Dodecyl Myristate | 6.00 |
| Titanium Dioxide | 1.00 |
| Octocrylene | 7.00 |
| BHA | 0.20 |
| Methylparaben | 0.10 |
| Phase B | |
| Glycerin | 5.00 |
| Water | QS100 |
| Carbomer 940 | 0.30 |
| Phase C | |
| Triethanolamine 99% | 0.30 |
| Phase D | |
| Water | 2.00 |
| Imidizolidinyl Urea | 0.30 |

[1]Available as Apifac from Gattefosse S.A.

Combine and heat Phase A ingredients to 75° C. Next disperse the carbomer into the water and glycerin and heat this Phase B to 75° C. and mix into Phase A to form the emulsion. Add Phase C with high speed stirring and cool to 40° C. Combine Phase D ingredients until dissolved and add to the emulsion.

This sunscreen water-in-oil emulsion is useful for topical application to the skin to provide protection from the harmful effects of ultraviolet radiation.

EXAMPLE VI

Sunscreen Oil

A sunscreen oil is prepared by combining the following components utilizing conventional mixing techniques.

| Ingredients | % Weight |
| --- | --- |
| Phase A | |
| Mineral Oil | QS100 |
| Octocrylene | 7.00 |
| Titanium Dioxide | 0.10 |
| Sesame Oil | 15.00 |
| Isopropyl Myristate | 2.00 |
| Sorbitan Oleate | 1.50 |
| Propylparaben | 0.50 |
| D&C Red #17 | 0.002 |

The above ingredients are combined and heated until the propylparaben is dissolved.

This sunscreen oil is useful for topical application to the skin to provide protection from the harmful effects of ultraviolet radiation.

EXAMPLE VII

Anhydrous Sunscreen Gel

An anhydrous sunscreen gel is prepared by combining the following components utilizing conventional mixing techniques.

| Ingredients | % Weight |
| --- | --- |
| Phase A | |
| Mineral Oil | QS100 |
| Octocrylene | 7.00 |
| Titanium Dioxide | 0.50 |
| Petrolatum | 15.00 |
| Paraffin Wax | 10.00 |
| Ozokerite | 8.00 |
| Isopropyl Myristate | 5.00 |
| Fragrance | 0.50 |
| D&C Yellow #10 Aluminum Lake and Mineral Oil and Petrolatum[1] | 0.545 |
| D&C Red #17 | 0.0055 |
| Propylparaben | 0.100 |
| Butylparaben | 0.03 |

[1]Available as Opatint Yellow OD-2169 from Colorcon.

The above ingredients are combined and heated with mixing until dispersed.

This anhydrous sunscreen gel is useful for topical application to the skin to provide protection from the harmful effects of ultraviolet radiation.

EXAMPLE VIII

Hydroalcoholic Sunscreen Gel

A hydroalcoholic sunscreen gel is prepared by combining the following components utilizing conventional mixing techniques.

| Ingredients | % Weight |
| --- | --- |
| Phase A | |
| Water | QS100 |
| Hydroxyethyl cellulose | 0.90 |
| TEA-Coco-Hydrolyzed Animal Protein | 2.00 |
| Hydrolyzed Animal Collagen[1] | 1.00 |
| Octocrylene | 3.00 |
| Titanium Dioxide | 0.10 |
| Glycerin | 1.00 |

| Ingredients | % Weight |
|---|---|
| Phase B | |
| Soluble Animal Collagen[1] | 3.00 |
| Phase C | |
| Alcohol SD-40 | 20.00 |
| Polysorbate 20 | 0.80 |
| Fragrance | 0.50 |

[1]Available as Polypro 5000 from Geo. A. Hormel & Co.
[2]Available as Sollagen from Geo. A. Hormel & Co.

Heat water to 60°–65° C. and sprinkle the hydroxyethyl cellulose into the stirred water. Allow to fully dissolve to a clear solution. Stop heating and add remaining Phase A ingredients. Cool to below 35° C. and add Phase B. Mix Phase C ingredients and add to the mixture of Phases A and B.

This hydroalcoholic gel is useful for topical application to the skin to provide protection from the harmful effects of ultraviolet radiation.

EXAMPLE IX

Lip Protecting Stick

A lip protecting stick is prepared by combining the following components utilizing conventional mixing techniques.

| Ingredients | % Weight |
|---|---|
| Phase A | |
| Mineral Oil | QS100 |
| Octocrylene | 7.00 |
| Titanium Dioxide | 1.00 |
| Petrolatum | 15.94 |
| $C_{12-15}$ Alcohols Benzoate | 13.00 |
| Ozokerite Wax | 13.00 |
| Candilila Wax | 13.00 |
| Oleyl Alcohol | 8.00 |
| Tocopheryl Acetate | 1.00 |
| Propylparaben | 0.10 |

The ingredients are combined together and heated with mixing until uniform, and the resulting mixture is poured into appropriate containers and allowed to harden.

This lip protecting stick is useful for topical application to the lips to provide protection from the harmful effects of ultraviolet radiation.

EXAMPLE X

Sunscreen Spray Emulsion Lotion

A sunscreen spray emulsion is prepared by combining the following components utilizing conventional mixing techniques.

| Ingredients | % Weight |
|---|---|
| Phase A | |
| Water | QS100 |
| Carbomer 1342 | 0.10 |
| Disodium EDTA | 0.10 |
| Phase B | |
| Octocrylene | 7.00 |
| Titanium Dioxide | 0.10 |
| PVP Eicosene Copolymer | 1.00 |
| Stearic Acid | 0.15 |
| Simethicone | 0.01 |
| Stearoxy Dimethicone | 0.50 |
| Phase C | |
| Water | 2.00 |
| Triethanolamine (99%) | 0.175 |
| Phase D | |
| Water | 2.00 |
| Butylene Glycol | 2.00 |
| DMDM Hydantoin (and) Iodopropynyl Butylcarbamate | 0.25 |
| d,1 Panthenol | 0.50 |
| Phase E | |
| $C_{12-15}$ Alcohols Benzoate | 0.50 |
| Fragrance | 0.30 |
| Cyclomethicone | 2.00 |

The emulsion is made using the general procedure given in Example I except that this formula does not contain DEA-cetyl phosphate and the Phase E ingredients are combined together before adding.

This sunscreen spray emulsion is useful for topical application to the skin to provide protection from the harmful effects of ultraviolet radiation.

EXAMPLE XI

The ability of the compositions of the present invention to protect skin, i.e. UV absorption after water resistance testing, was evaluated. The water resistance of a composition embodying the present invention was evaluated on a collagen film substrate, via absorbance of UV radiation between 290–400 nm, with a Phillips 8800 Dual Beam spectrophotometer equipped with an integrating spheroid. An appropriate substrate for evaluating the suncare formulations of the instant invention should have surface properties which attempt to simulate those of human skin and should also have a relatively low UV absorbance in the 290–400 nm region compared to the suncare samples to be evaluated. Collagen film was employed since this material met these requirements. The collagen film material used as a substrate for the evaluation of the instant invention was obtained from Semex Medical (Frazer, PA).

In order to evaluate the individual and combined contributions of both the titanium dioxide and the octocrylene the following formulations were prepared: (A) an Emulsion base containing 7% octocrylene (i.e., the composition described in Example III minus the titanium dioxide); (B) an Emulsion base containing 1% titanium dioxide (i.e. Example III minus octocrylene); (C) an Emulsion base containing both 1% titanium dioxide and 7% octocrylene (i.e. Example III). These formulations were evaluated on the collagen film substrate at a dosage of 2 mg/cm$^2$. The treated substrates were immersed in a gently stirred water bath at 25° C. for 6 hours. After removal from the water bath and air drying, the samples were interposed between the UV radiation source and the integrating spheroid in the spectrophotometer. The absorption for each formulation was determined on multiple sites on the collagen film over the region from 290–400 nm, at 5 nm intervals. The mean absorbance at each wavelength was calculated. In order to determine the performance of Emulsion (C) containing octocrylene and titanium dioxide, the mean absorbance for this formulation was compared to the theoretical sum of that obtained on the individual sunscreen components, i.e. Emulsions (A) and (B). To determine the theoretical sum of the mean absorbance for Emulsions (A) and (B) the mean absorbance for these two formulations at each wavelength interval was summed. The mean absorbance at each wavelength for the actual octocrylene/titanium dioxide formulation [i.e. Emulsion (C)], and for the theoretical octocrylene/titanium dioxide formulation, [i.e. the sum of Emulsions (A) and (B)], were converted to percent absorption using the following equations:

$$\% Transmission = 10^{-Absorbance} \times 100 \text{ and}$$

$$\% Absorption = 100 - \% Transmission$$

The mean %Absorption over the entire wavelength range of 290–400 nm was then calculated for the actual octocrylene/titanium dioxide formulation [i.e. Emulsion (C)], and for the theoretical octocrylene/titanium dioxide formulation, [i.e. the sum of Emulsions (A) and (B)] from the individual %Absorption values.

TABLE A

| Formula | Mean % Absorption |
| --- | --- |
| C 1% Titanium Dioxide + 7% Octocrylene | 66.31 |
| Theoretical Combination from absorption measurements on formulas A and B | 62.57 |
| | Wilcoxson $p < 0.017$ |

As seen in Table A, a greater than additive mean percent absorption was found when the mean percent absorption of Emulsion C (66.31%) was compared with the theoretically expected mean percentage absorption calculated from the theoretical combination of Emulsions A and B (62.51%). This difference in %Absorption was determined to be statistically significant; $p < 0.017$ from Wilcoxson test. Therefore, a product containing the combination of octocrylene and titanium dioxide would provide a higher level of water-proof sun protection from damaging UV radiation than expected based on the theoretical sum of these two sunscreen components.

What is claimed is:

1. A suncare composition having enhanced substantivity and efficacy comprising:
    (a) a sunscreen component consisting essentially of:
        (i) from about 0.1% to about 20% of octocrylene based on the weight of the total composition;
        (ii) from about 0.1% to about 25% of titanium dioxide based on the weight of the total composition; and
        (iii) from about 0.5% to about 20% of a sunscreen compound based on the weight of the total composition selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, homomenthyl salicylate, octyl salicylate, butylmethoxydibenzoylmethane, 4-isopropyl dibenzoylmethane, benzylidene camphor, 4-methylbenzylidene camphor, 4-N,N-(2-ethylhexyl)methylaminobenzoic acid ester of 2,4-dihydroxybenzophenone, 4-N,N-(2-ethylhexyl)methylaminobenzoic acid ester with 4-hydroxydibenzoylmethane, 4-N,N-(2-ethylhexyl)methylaminobenzoic acid ester of 2-hydroxy-2-(2-hydroxyethoxy)benzophenone, 4-N,N-(2-ethylhexyl)-methylaminobenzoic acid ester of 4-(2-hydroxyethoxy)dibenzoylmethane, zinc oxide, silica, tron oxide and mixtures thereof; and
    (b) a safe and effective amount of a topical carrier.

2. A suncare composition according to claim 1 wherein said topical carrier is an anhydrous liquid solvent.

3. A suncare composition according to claim 1 wherein said topical carrier is an aqueous-based, single-phase liquid solvent.

4. A suncare composition according to claim 1 wherein said topical carrier is an anhydrous solid.

5. A suncare composition according to claim 1 having from about 3% to about 10% octocrylene and from about 0.5% to about 5% titanium dioxide.

6. A suncare composition according to claim 5 wherein said topical carrier is an emulsion.

7. A suncare composition according to claim 6 wherein said emulsion is an oil-in-water emulsion.

8. A suncare composition according to claim 1 having from about 3% to about 7% octocrylene and from about 1% to about 4% titanium dioxide.

9. A suncare composition according to claim 8 wherein said topical carrier is an emulsion.

10. A suncare composition according to claim 9 wherein said emulsion is an oil-in-water emulsion.

11. A suncare composition according to claim 1 wherein said topical carrier is an emulsion.

12. A suncare composition according to claim 11 wherein said emulsion is a water-in-oil emulsion.

13. A suncare composition according to claim 11 wherein said emulsion is a water-in-oil-in-water emulsion.

14. A suncare composition according to claim 11 wherein said emulsion is an oil-in-water-in-silicone emulsion.

15. A suncare composition according to claim 11 wherein said emulsion is an oil-in-water emulsion.

16. A method for providing enhanced protection to the skin of humans or lower animals from the effects of ultraviolet radiation, said method comprising topically applying to the skin of the human or lower animal an effective amount of a suncare composition according to claim 1.

17. A method for providing enhanced protection to the skin of humans or lower animals from the effects of ultraviolet radiation, said method comprising topically applying to the skin of the human or lower animal an effective amount of a suncare composition according to claim 11.

18. A method for providing enhanced protection to the skin of humans or lower animals from the effects of ultraviolet radiation, said method comprising topically applying to the skin of the human or lower animal an effective amount of a suncare composition according to claim 10.

19. A method for providing enhanced protection to the skin of humans or lower animals from the effects of ultraviolet radiation, said method comprising topically applying to the skin of the human or lower animal an effective amount of a suncare composition according to claim 2.

20. A method for providing enhanced protection to the skin of humans or lower animals from the effects of ultraviolet radiation, said method comprising topically applying to the skin of the human or lower animal an effective amount of a suncare composition according to claim 3.

* * * * *

UNITED STATES PATENT AND TRADEMARK OFFICE
CERTIFICATE OF CORRECTION

PATENT NO. : 5,306,485

DATED : April 26, 1994

INVENTOR(S) : Larry R. Robinson et al.

It is certified that error appears in the above-identified patent and that said Letters Patent is hereby corrected as shown below:

At column 1, line 22 "day-today" should read --day-to-day--.

At column 3, line 4 "about I" should read --about 1--.

At column 3, line 28 "250° C." should read --25° C.--.

At column 3, line 45 "–10° C. octocrylene" should read ---10° C. Octocrylene--.

At column 3, line 56 "107.," should read --10%,--.

At column 3, line 64 "about I nm" should read --about 1 nm--.

At column 4, line 58 "an hydrous" should read --anhydrous--.

At column 5, line 6 "99.87. by" should read --99.8% by--.

At column 5, line 26 "(W/w)" should read --(w/w)--.

At column 6, line 6 insert

--wherein $\sum_i E_i$ = the sum of the heat of vaporization additive group contributions $\sum_i m_i$ = the sum of the molar volume additive group contributions--.

At column 6, line 26 "(cal/CM$^3$)$^{\frac{1}{2}}$" should read --(cal/cm$^3$)$^{\frac{1}{2}}$--.

At column 6, line 29 "kj/mol" should read --kJ/mol--.

At column 7, line 49 "I MED" should read --1 MED--.

At column 7, line 52 "I MED" should read --1 MED--.

UNITED STATES PATENT AND TRADEMARK OFFICE
CERTIFICATE OF CORRECTION

PATENT NO. : 5,306,485
DATED : April 26, 1994
INVENTOR(S) : Larry R. Robinson et al.

It is certified that error appears in the above-identified patent and that said Letters Patent is hereby corrected as shown below:

At column 10, line 56 "diesters Of" should read --diesters of--.

At column 11, line 45 "I-eicosene" should read --1-eicosene--.

At column 19, line 63 "2-(2-hydroxyethoxy)" should read --4-(2-hydroxyethoxy)--.

At column 19, line 66 "tron oxide" should read --iron oxide--.

Signed and Sealed this

Twenty-seventh Day of April, 1999

Attest:

Q. TODD DICKINSON

Attesting Officer     Acting Commissioner of Patents and Trademarks